(12) United States Patent
Jussel

(10) Patent No.: US 9,784,501 B2
(45) Date of Patent: Oct. 10, 2017

(54) DENTAL FURNACE

(71) Applicant: Ivoclar Vivadent AG, Schaan (LI)

(72) Inventor: Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 497 days.

(21) Appl. No.: 14/367,299

(22) PCT Filed: Nov. 7, 2013

(86) PCT No.: PCT/EP2013/073287
§ 371 (c)(1),
(2) Date: Jun. 20, 2014

(87) PCT Pub. No.: WO2014/090487
PCT Pub. Date: Jun. 19, 2014

(65) Prior Publication Data
US 2014/0339216 A1   Nov. 20, 2014

(30) Foreign Application Priority Data

Dec. 13, 2012   (EP) .................................... 12197055

(51) Int. Cl.
*F27B 5/14* (2006.01)
*F27B 17/02* (2006.01)
(Continued)

(52) U.S. Cl.
CPC ............ *F27B 17/025* (2013.01); *A61C 13/20* (2013.01); *F27B 5/18* (2013.01); *F27D 11/02* (2013.01); *F27D 19/00* (2013.01); *F27D 21/0014* (2013.01); *F27D 21/02* (2013.01); *F27B 2005/068* (2013.01); *F27D 2019/0003* (2013.01)

(58) Field of Classification Search
CPC .. F27B 17/025; F27B 5/18; F27B 5/04; F27B 5/08; F27B 5/14; F27B 2005/068; A61C 13/20; F27D 19/00; F27D 11/02; F27D 21/0014; F27D 21/02; F27D 21/0017; F27D 2019/0003
See application file for complete search history.

(56) References Cited

U.S. PATENT DOCUMENTS

| 5,788,485 A | 8/1998 | Gruenenfelder et al. |
| 2003/0234095 A1 | 12/2003 | Usui |
| (Continued) | | |

FOREIGN PATENT DOCUMENTS

| CA | 2340805 A1 | 9/2001 |
| DE | 19754077 A1 | 6/1999 |
| (Continued) | | |

*Primary Examiner* — Shawntina Fuqua
(74) *Attorney, Agent, or Firm* — Ann M. Knab; Thad McMurray

(57) ABSTRACT

The invention concerns a dental furnace, with a furnace base and with a furnace hood, wherein the furnace hood includes a firing chamber for the accommodation of dental restorations, with a temperature sensor that records the temperature of the dental restoration and which is connected to a control device which controls the dental furnace, and the dental furnace (10) includes a drive unit (18) for the furnace hood (16) and the control device (30) controls the drive unit (18) based on the temperature recorded by the temperature sensor (20), namely opens the furnace hood.

14 Claims, 2 Drawing Sheets

(51) Int. Cl.
*A61C 13/20* (2006.01)
*F27B 5/18* (2006.01)
*F27D 11/02* (2006.01)
*F27D 19/00* (2006.01)
*F27D 21/00* (2006.01)
*F27D 21/02* (2006.01)
F27B 5/06 (2006.01)

(56) References Cited

U.S. PATENT DOCUMENTS

| | | |
|---|---|---|
| 2005/0250067 A1 | 11/2005 | Rohner et al. |
| 2009/0246739 A1 | 10/2009 | Jussel et al. |
| 2010/0047731 A1* | 2/2010 | Zubler .................. A61C 13/20 432/45 |
| 2013/0026157 A1 | 1/2013 | Jussel et al. |
| 2013/0029280 A1 | 1/2013 | Jussel et al. |

FOREIGN PATENT DOCUMENTS

| | | |
|---|---|---|
| DE | 102006004433 A1 | 8/2007 |
| DE | 102006032655 A1 | 1/2008 |
| EP | 2550928 A1 | 1/2013 |
| EP | 2551621 A1 | 1/2013 |
| JP | H06123556 A | 5/1994 |
| JP | H08059247 | 8/1994 |
| JP | 2002277176 A | 9/2002 |
| RU | 2063727 C1 | 7/1996 |

* cited by examiner

DENTAL FURNACE

CROSS-REFERENCE TO RELATED APPLICATIONS

This application is a National Stage application of International patent application PCT/EP2013/073287 filed on Nov. 7, 2013, which claims priority to European patent application No. 12197055.2 filed on Dec. 13, 2012, the disclosures of which are incorporated herein by reference in their entirety.

TECHNICAL FIELD

The invention concerns a firing or pressing furnace for dental restorations having a furnace base, a furnace hood, wherein the furnace hood includes a firing chamber for the accommodation of dental restorations and a drive unit for the relative movement between the furnace hood and the furnace base, with a temperature sensor that records the temperature of the dental restorations and which is connected to a control device which controls the dental furnace.

BACKGROUND OF THE INVENTION

Such dental furnaces for firing and, if applicable, pressing dental restoration parts have been known for a long time. In such dental furnaces, a dental restoration part is, or a number of dental restoration parts are, subjected to firing process or a pressing process, which is controlled by a program in accordance with predetermined temperature and, if applicable, pressing profiles.

The quality of the dental restoration parts produced considerably depends on that the parameters intended and adapted to the dental restoration material present are exactly adhered to during the firing and, if applicable, the pressing process. These do not only include the temperature profile to be adhered to, but also, for instance, the pressure conditions existing during the firing cycle.

Such dental restoration parts include dental restoration parts to be produced out of plastics, of metals, of composites, and in particular also of ceramics or of combinations of these dental.

The materials to be processed, the size, as well as the number and shape of dental restoration parts to be produced simultaneously determine, among other things, the overall heat capacity of the dental restoration parts to be processed. Thus, an adaptation of the heating power can become necessary, for which purpose different processing programmes can be activated at these firing or pressing furnaces via an input device, in which programmes optimum operation parameters for the respective circumstances (material, size, etc.) are stored. By activating and starting the suitable processing programme, a firing process for achieving an optimum quality in the product is aimed at.

Such dental furnaces essentially include a furnace base on which the dental restoration parts to be fired are accommodated, if applicable inside a muffle, a furnace hood which accommodates, besides a thermal insulation, in most cases also the heating device (e.g. electric heating coils), and a control device with a display and input device connected to it. The control device further comprises a memory device in which the processing programmes are stored. The input device for its part can be combined partly with the display device in the form of a touch-sensitive display (touch screen) and can furthermore as well comprise buttons ("soft keys") that are in a basically known fashion provided with a firm function or with a function changeable via the display.

Such a dental furnace is, for example, described in DE 197 54 077 B4. On a display device, parameters can be displayed both numerically and in differently coloured depictions of curves which can be overlaid on one another. Input is possible via buttons, which allows to modify a firing programme if necessary.

Moreover, it has been suggested lately to equip dental furnaces also with a camera which is preferably also sensitive for the IR spectrum, and thus be able to record the temperature of the objects to be fired already during their placement in the furnace too. This has the advantage, among others, that a rather precise recording of the actual temperature, for instance of the muffle which was pre-heated in a pre-heating furnace in advance, can be achieved. By taking into account the actual temperature of the muffle, the processing programme of the dental furnace selected, for instance a pressing programme, can then be adapted and thus an improved result can be achieved.

Such recording of temperature has been suggested in such a fashion that based on an absolute temperature of the muffle thus recorded, a correction of the firing parameters, such as, for example, the duration of pre-heating, can be made in order to be able to guarantee optimum processing parameters for the material to be processed in the subsequent processing step.

Despite the sometimes rather complex control of the furnace parameters during the firing process, which takes into account, besides the actual firing temperature (or the firing curve), the introduction temperature of the dental restoration parts to be fired as well as the specifics of the materials to be fired, it has turned out that the firing results and the quality, respectively, of the dental restorations thus manufactured do not always meet the expectations.

SUMMARY OF THE INVENTION

In contrast, the invention is based on the task of creating a dental furnace in accordance with the preamble of claim 1 as well as a process in accordance with claim 16, with the help of which the high quality expectations, such as a high degree of dimensional accuracy and longevity of the dental restoration parts to be produced can be fulfilled.

This task is solved in accordance with the present invention by claim 1 as well as claim 16. Advantageous embodiments result from the subordinate Claims.

Some of the known dental furnaces are equipped with a motor-activated furnace hood. This allows for automatic closure of the furnace hood at the beginning of the firing programme as well as a very low-vibration opening at the end of the firing cycle.

A stationary furnace hood with a furnace base which can be lowered with the help of a motor is basically just as suitable, however, this solution has the disadvantage that the freshly fired dental restoration parts are inevitably subjected to vibrations when the furnace base is lowered. The extent of vibrations depends on the construction and the quality of the gear used for driving the furnace base. In any case, however, these vibrations have adverse effects on the product quality of the dental restoration part which is still in the process of cooling down.

Insofar, a furnace hood which can be opened with the help of a motor and a stationary furnace base are assumed here. The principle of the present invention, however, can also be used without any problem with the above-mentioned movable furnace base in connection with a stationary furnace hood.

In the search for ways to improve product quality it has been discovered that besides such parameters as optimum firing temperature and firing time, there are further circumstances which are of essential importance for the optimum quality of the dental restoration parts to be produced. The process of cooling down of the ready-fired dental restoration parts has a very large influence on the long-term quality, too. For instance, cooling down too rapidly, such as can be caused by directly taking out the object to be fired from the firing furnace immediately after the actual firing process is finished, can lead to tensions inside the objects to be fired which can result in distortion and thus poor dimensional accuracy or in extreme cases even in stress cracks.

Herein, such stress cracks may appear in the worst case only a long time after production as a result of use and punctual strains on the dental restorations occurring in use.

Cooling down the dental restoration part too slowly does not have any detrimental effect on product quality at first sight, although the cycle time is prolonged during which the firing furnace concerned is not available for another firing cycle, and it is insofar not desirable.

Cooling down too quickly, which can for example be carried out by accelerating the cooling process with the help of a ventilator provided inside the dental furnace, in contrast, can cause the problems described above, and for this reason it is to be avoided wherever possible.

In certain cases in which the dental furnace is supposed to be operated with negative pressure or a vacuum inside, or also with a controlled atmosphere, a ventilator must moreover not be used since ventilation apertures, even if they were closable, counteract the formation of a negative pressure or even a vacuum.

The cooling process of the object to be fired varies depending on its mass, size and shape (e.g. due to different surface structures). If the ratio between surface content and volume of the object to be fired is too large, this results in a higher cooling-down rate compared with a lower surface content relative to the volume of the object to be fired. Moreover, the supports of the objects to be fired, firing pegs and support pastes which may be used as well as the furnace hood and furnace base each contribute to a modification of the cooling-down rate.

In accordance with the present invention, it is also favourable that variations in ambient conditions of the furnace can also be compensated for in accordance with the present invention. Thus, the temperature sensor in accordance with the present invention, which can be provided as an infrared camera, records increased cooling due to a lower ambient temperature, and the control of the furnace hood drive unit in accordance with the present invention makes it possible to realise an adaptation based on the temperature gradient, in case the cooling process is too rapid, for example by opening the furnace hood more slowly or closing it again a little.

Even if the dental furnace in accordance with the present invention is described with a stationary furnace base and a furnace hood movable relative to the former, it is to be understood that alternatively the furnace hood can be stationary too and the furnace base can be provided in such a form that it can be lowered. Thus, the drive unit for the furnace hood is to be understood as the drive unit for the relative movement between furnace hood and furnace base, and opening the furnace hood is to be understood as the relative movement of the latter with respect to the furnace base.

An individual, speedy, but yet controlled (i.e. by no means too rapid) cooling of the objects to be fired upon completion of the firing process under consideration of the factors mentioned above, which at the same time avoids the disadvantages of the accelerated cooling with the help of a ventilator integrated in the furnace hood as mentioned above, is thus desirable.

The above disadvantages, such as the likeness of thermally or mechanically induced stress cracks, or too long cycle times caused by excessively prolonged cooling can be avoided in a surprisingly easy fashion with the help of the solution in accordance with the present invention which is described more closely in the following.

With the help of a temperature recording device positioned outside the firing chamber, which is preferably formed by an infrared or IR camera, the temperature of the dental restoration part or the support of the object to be fired, such as for instance a muffle in which the object to be fired is accommodated, can be recorded during insertion into the dental furnace, as mentioned above, as long as the furnace hood is not yet completely closed. Advantageously, this temperature recording device is positioned in such a fashion that it still has direct optical contact with the object to be fired inside the furnace even if the furnace hood is opened only very little.

For the period of time which extends from insertion of the object to be fired into the firing chamber and/or its being positioned on the furnace base until the complete closure of the furnace hood (i.e. until the furnace hood blocks the "view" of the object to be fired for the IR camera), the temperature can insofar be continuously recorded. By recording the temperature in relation to time, a temperature profile or temperature gradient can thus be recorded.

Measuring the temperature of the firing chamber when the furnace hood is completely closed is then of course only possible with the help of the temperature sensor positioned inside the firing chamber (e.g. a thermal element).

With the help of a window which is thermally insulating, but if possible not depressing IR radiation and thus insofar permeable for IR radiation and which is positioned within the optical path between the object to be fried and the IR camera inside the furnace hood, a measurement of the temperature of the object to be fired would even be possible with the furnace hood completely closed.

Upon completion of the firing process, the heating of the furnace is switched off in accordance with the programme, and the cooling down of the object to be fired is begun. In order to accelerate the cooling process, without, however, having to use technical means, such as a ventilator, it is possible in a surprisingly simple fashion to open the furnace hood controlled via the control device of the furnace with the help of the motor and again record the temperature of the object to be fired via the IR camera positioned outside the firing chamber.

The continuous recording of the temperature of the object to be fired can thus begin in the very moment in which the furnace hood is opened to a sufficient degree in order to allow optical contact between the IR camera and the object to be fired. As described above, the temperature gradient with which the cooling process of the object to be fired is advancing can now be recorded.

If the furnace hood is opened farther, this will lead to a more rapid cooling down, since the radiation of the residual heat stored in the furnace hood and its insulation to the object to be fired, which is thus farther apart from the furnace hood, is reduced, and an improved heat transfer between the ambient air and the object to be fired can take place. If the furnace hood is not so widely opened, in contrast, the radiation of residual heat from the heating and insulation to the object to be fired allows the latter to post-heat, moreover, if the furnace hood is closed relatively far, a temperature equalisation between the surroundings and the object to be fired is hindered. The cooling curve is distinctly flatter in this case.

With the help of the control device of the dental furnace, a continuous comparison of the actual cooling-down rate of the object to be fired with the optimum cooling-down rate predetermined in the firing profile of the processing programme selected is possible. By controlling the furnace hood motor with the help of the control device of the furnace, an adaptation of the cooling-down rate of the object to be fired can now be realised in a surprisingly simple fashion in such a way that by decreasing the opening of (i.e. lowering) the furnace hood, this can be reduced, or by increasing the opening of (i.e. elevating) the furnace hood, the cooling-down rate can be increased.

For different temperature ranges, this optimum cooling-down rate of the object to be fired can very well be different. By opening or lowering the furnace hood controlled by the programme, it is possible to realise a higher cooling-down rate for the beginning of the cooling process, for instance, then distinctly reduce it when passing through what is referred to as the transformation temperature which represents the critical transition of a ceramic or glass from the flexible to the solid state, in order to subsequently have a faster, as less critical, cooling process be carried out again.

When a final cooling temperature has been reached, which is also predetermined in the firing profile of the processing programme, a signal is then output by the furnace indicating that the object to be fired can now be removed, and the furnace hood is opened completely, if this has not been done before.

As a result of the automatic control of the opening position of the furnace hood in accordance with the present invention and depending on the actual temperature of the object to be fired, it is possible in accordance with the present invention to realise an optimum cooling of the object to be fired with a cycle time that is as short as possible, without having to fear the detrimental effects of a cooling happening too rapidly, such as, for instance, thermal tensions (distortion, cracks).

Dental furnace in accordance with claim 1, characterised in that the temperature sensor (20) continuously records the temperature of the dental restoration, and in that the control device (30) calculates a temperature gradient from the continuously recorded temperature values of the temperature sensor (20).

In accordance with a favourable embodiment, it is intended that the temperature sensor continuously records the temperature of the dental restoration, and that the control device calculates a temperature gradient from the continuously recorded temperature values of the temperature sensor.

In accordance with an advantageous embodiment, it is intended that the temperature sensor is an optical sensor, in particular an infrared sensor.

In accordance with an advantageous embodiment, it is also intended that the temperature sensor is a two-dimensional sensor array, in particular a thermographic camera.

In accordance with an advantageous embodiment, it is also intended that the temperature sensor is positioned outside the firing chamber, in particular laterally above the furnace base.

In accordance with a further advantageous embodiment, it is intended to be characterised in that the furnace hood is provided with a window transparent for IR radiation which is positioned within the optical path between the dental restoration accommodated inside the firing chamber and the temperature sensor.

In accordance with an advantageous embodiment, it is also intended to be characterised in that the control device is suitable for controlling the cooling-down rate of the dental restoration by means of changing the position of the furnace hood relative to the furnace base with the help of the drive unit.

In accordance with an advantageous embodiment, it is intended that the temperature of a carrier of the object to be fired can be recorded with the help of the temperature sensor.

In accordance with an advantageous embodiment, it is further intended that also the ambient temperature as well as the dimensions of the dental restoration and/or a muffle which accommodates the dental restoration can be recorded with the help of the temperature sensor.

In accordance with an advantageous embodiment, it is intended that processing programmes can be selected with the help of an operation device, which processing programmes can be stored in the control device, and target values for a cooling-down rate of the dental restoration are predetermined in the processing programmes.

In accordance with an advantageous embodiment, it is intended that the control device is suitable for lowering the furnace hood if the cooling-down rate of the dental restoration is to high compared with the target value predetermined by the selected processing programme, and that the control device is suitable for elevating or accelerating the furnace hood if the cooling-down rate of the dental restoration is too low compared with the target value predetermined by the selected processing programme.

In accordance with an advantageous embodiment, it is intended that a heating device is provided inside the furnace hood, and that the control device is suitable for switching on the heating device if the cooling-down rate of the dental restoration is too high compared with the target value predetermined by the selected processing programme.

In accordance with an advantageous embodiment, it is further intended that a cooling device is provided at the dental furnace, and that the control device is suitable for switching on the cooling device if the cooling-down rate of the dental restoration is too low compared with the target value predetermined by the selected processing programme.

In accordance with an advantageous embodiment, it is intended that the dental furnace further comprises a signalling device connected to the control device, and that the control device is suitable via the signalling device to signal the deviation below a cooling-down temperature of the dental restoration part predetermined by the selected processing programme.

In accordance with an advantageous embodiment, it is intended that the temperature sensor also records the presence or absence of the dental restoration and the moment of its removal and forwards the result of the recording to the control device which in particular stores this.

In accordance with a further advantageous embodiment, it is intended that the dental furnace is provided with a furnace base and a furnace hood which can be moved with the help of a drive unit, and the furnace hood includes a firing chamber for the accommodation of dental restorations, and the dental furnace is further provided with a temperature sensor which is connected to a control device and which is positioned outside the firing chamber, and that the control device opens the furnace hood after expiry of a completed firing process corresponding to a predetermined value stored in the control device; the temperature sensor records the temperature of the dental restoration; and if the temperature of the dental restoration recorded by the temperature sensor falls below a value stored in the control device, the control device completely opens the furnace hood with the help of the drive unit and/or outputs a signal to the user via a signalling device connected to the control device.

BRIEF DESCRIPTION OF THE DRAWINGS

Further advantages, details and features of an exemplary embodiment result from the Figures and the following description of the invention.

The Figures show.

DETAILED DESCRIPTION OF THE INVENTION

Figure 1:
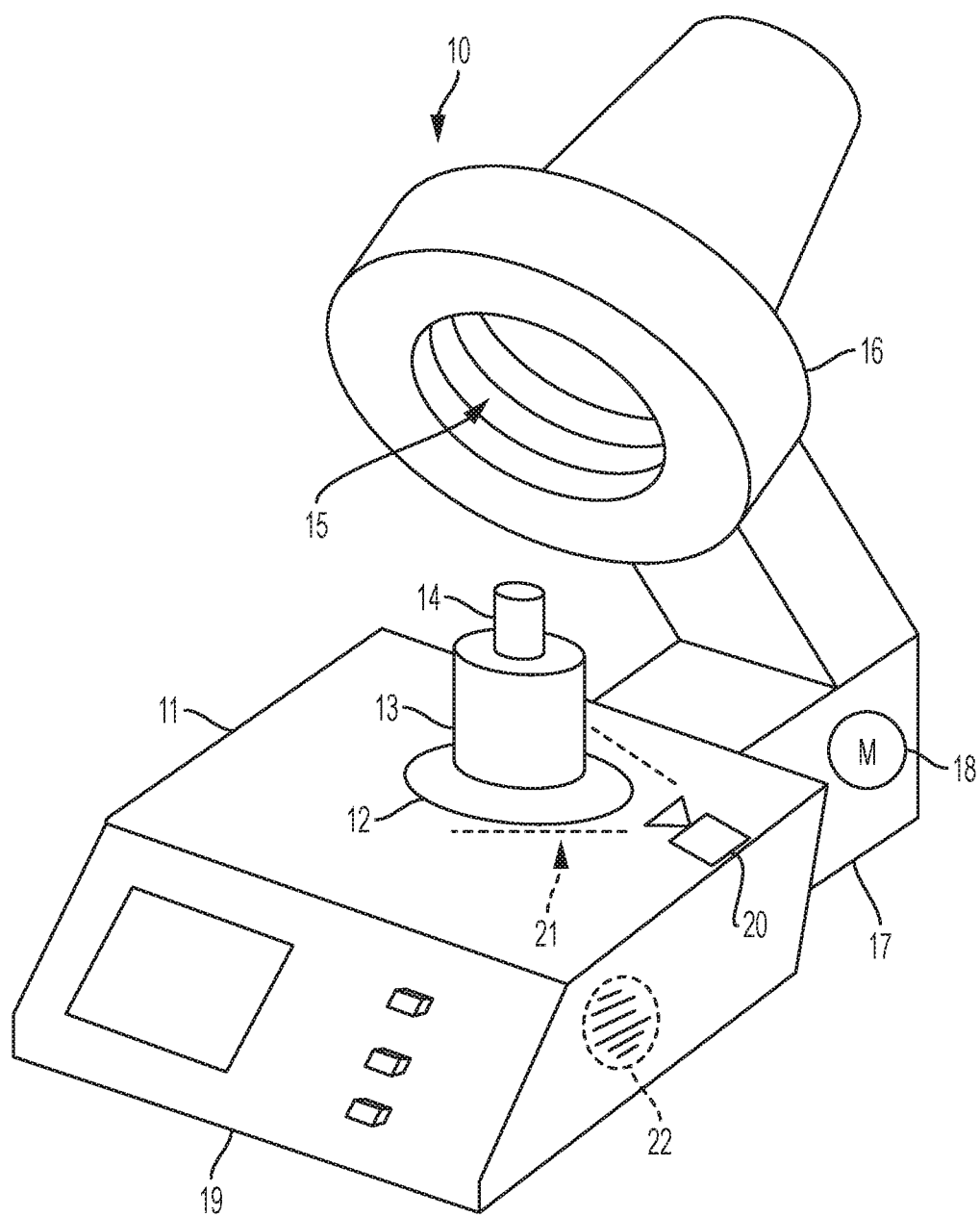
FIG. 1 a schematic view of the dental furnace in accordance with the present invention.

A dental furnace 10 comprises a furnace base 11 with a firing chamber bottom 12 which is destined to accommodate the object to be fired, for instance a muffle 13 (depicted here with workpiece 14 inserted). For firing, the object to be fired is accommodated in a firing chamber 15 which is depicted only schematically in FIG. 1 and which is provided in furnace hood 16 that is connected with furnace base 11 with the help of a joint 17. The degree to which furnace hood 16 is opened is adaptable via motor 18 which is only hinted in FIG. 1 for reasons of clarity. If the dental furnace 10 in accordance with the present invention is a pressing furnace, it additionally comprises, preferably in furnace hood 16, a device for pressing the dental material to be processed, the depiction of which, however, has been omitted here for the sake of more clarity.

Dental furnace 10 comprises moreover an operation device 19 which works in combination with a control device that is not depicted in FIG. 1. Connected to the control device, there is an IR camera 20 on top of furnace base 11. Camera 20 is arranged in such a fashion that it is positioned outside furnace hood 16 when the latter is closed and its opening and closing is not inhibited, when furnace hood 16 is opened, however, an unhindered view on the object to be fired is guaranteed. The recording area 21 of camera 20 extends along furnace base 11 and firing chamber bottom 12 in such a fashion that muffle 13 placed on firing chamber bottom 12 is recorded in its entire diameter. Preferably, camera 20 is positioned in such a fashion that it can record at least a small portion of muffle 13 inserted even if furnace hood 16 is only opened to a minimum, and thus a temperature measurement is possible even if furnace hood 16 is opened only to a minimum.

In the state depicted in FIG. 1, furnace hood 16 (including firing chamber 15) is completely elevated, such that the object to be fired can be inserted and removed, respectively.

In a particularly favourable fashion, in accordance with the present invention, a recording of the dimensions of the object to be fired is possible, besides the recording of the temperature of the object to be fired, with the help of the IR camera which is a two-dimensional array of IR sensors. In this, the contrast between the hot areas recorded by the camera (dental restoration or muffle) and the cooler areas which represent the temperature of the ambient air is made use of. In addition, an easier recording of the ambient temperature is possible in this fashion, whose value can also be used in controlling the cooling-down rate of the object to be fired.

By recording the dimensions of the dental restoration or the muffle which accommodates the former, a conclusion to the mass and—if the material is known—thus to the heat capacity of the object to be fired is also possible in a rather reliable fashion. This additional parameter determined in that way can as well be used in controlling the cooling-down rate.

It is to be understood that for controlling the position of furnace hood 16 relative to furnace base 11, besides the absolute position, the velocity of the movement, i.e. of opening and/or closing, can also be controlled with the help of control device 30. When the position calculated by control device 30 in accordance with the parameters determined, such as the current temperature of the object to be fired as well as the current cooling-down rate of the object to be fired, has been reached, the furnace hood will remain in this position until a deviation exceeding a predetermined threshold value is determined by control device 30. Subsequently, a new correction is carried out, if necessary in compliance with an also predetermined holding time or pause which is supposed to prevent permanent re-adjustment of the hood's position. Control device 30 uses commonly known algorithms, such as PID control or the like, for the determination of the control variable, i.e. the opening of furnace hood 16 relative to furnace base 11.

Figure 2:
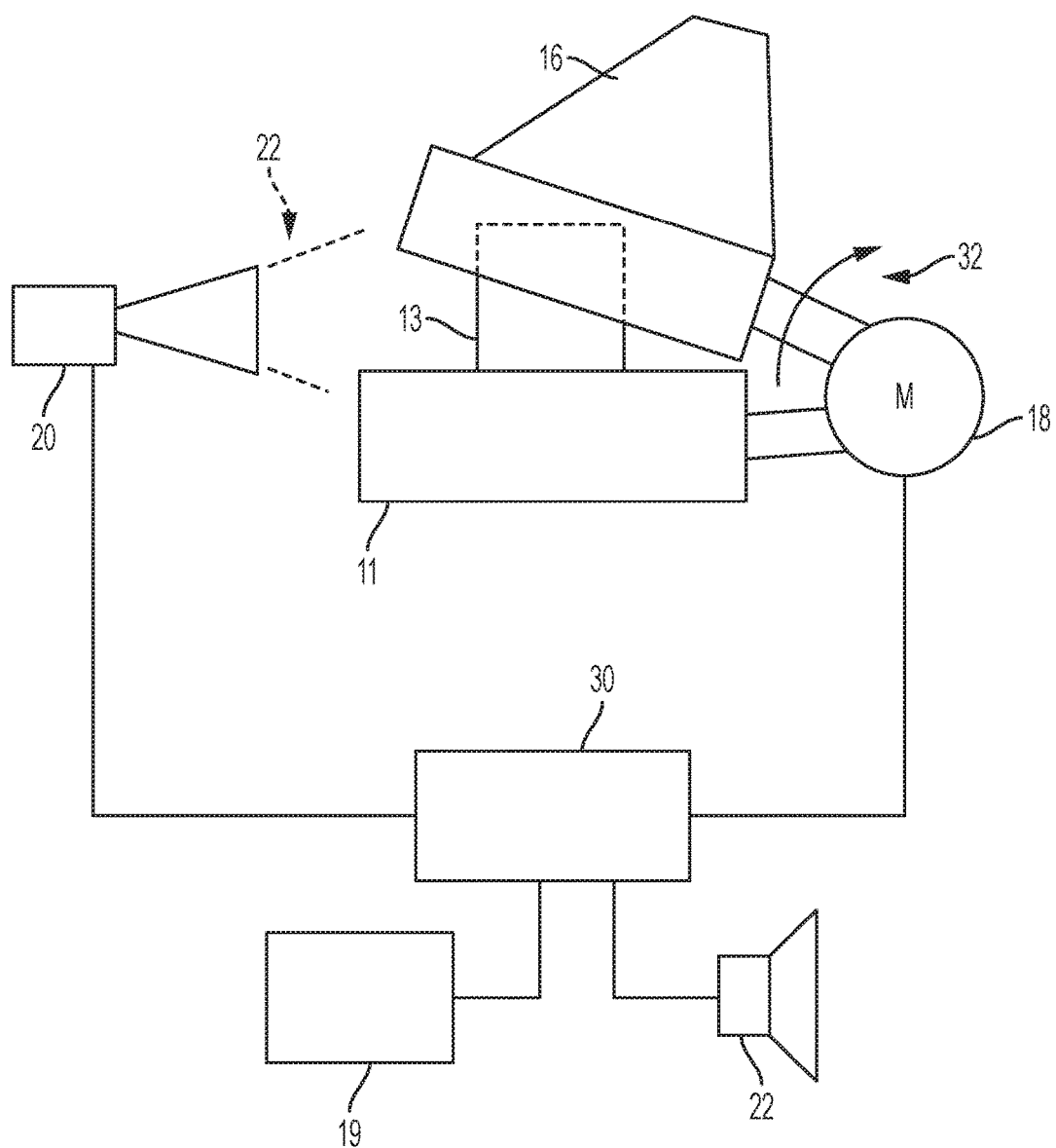
FIG. 2 a schematic view of the control of the position of the furnace hood during the controlled cooling process in the furnace in accordance with the present invention.

FIG. 2 schematically depicts the control of the position of furnace hood 16. With the help of the IR camera 20 that is positioned outside firing chamber 15, the temperature information recorded within its recording area 21 is transferred to control device 30. Since the temperatures of the object to be fired (e.g. the muffle) thus measured are recorded continuously over time, control device 30 can determine a temperature gradient and/or a cooling-down rate and compare it with a target value stored in the memory (not depicted) of the control device.

If this comparison results in a too low cooling-down rate, control device 30 will initiate a further opening of furnace hood 16 via motor 18, which is indicated by arrow 32 in FIG. 2. This makes possible an improved temperature equalisation between the air surrounding dental furnace 10 and muffle 13, the cooling-down rate will increase. If the cooling-down rate thus achievable were still not sufficient despite completely opened furnace hood 16, additional active cooling is possible with the help of further cooling measures, e.g. with the help of an external ventilator.

In the opposite case, if the cooling-down rate is determined to be too high, motor 18 is controlled in such a fashion with the help of control device 30 that furnace hood 16 is moved relatively towards furnace base 11. Thus, on the one hand, muffle 13 is subjected again to the radiation of the residual heat of the insulation (not depicted) positioned inside furnace hood 16, on the other hand, the temperature equalisation between the ambient air and muffle 13 is hindered, which will lead to a reduction in the cooling-down rate. If the residual heat stored in furnace hood 16 were not sufficient for reducing the cooling-down rate to the target value preset by the processing programme, additional heat energy may be introduced with the help of the firing chamber heating which is positioned inside furnace hood 16 and which is not depicted either for the sake of clarity.

The adaptation of the position of furnace hood 16 described above is done continuously in order to achieve a continuous control of the cooling-down rate of muffle 16. When a final temperature of the cooling down of muffle 16, that is also preset by the processing programme, has been reached, furnace hood 16 is opened completely by control device 30 with the help of motor 18, and in addition an acoustic signal is output via loudspeaker 22 or also optically via control panel 19, in order to give the user the information that the object to be fired can now be removed and dental furnace 10 is available for a new firing cycle.

Basically, it is also possible to recognize if the dental restoration part is taken out too early with the help of a temperature sensor. This holds true in particular if the temperature sensor is provided as a thermographic camera. In this embodiment, it is favourable to record in the style of a protocol at what temperature the dental restoration part has been removed in order to be able to record insofar the exact adherence to the removal temperature prescribed.

In an alternative embodiment, it is intended to adjust a firmly prescribed position of the furnace hood with the help of a motor on the basis of the known previous temperature treatment (firing temperature, heat capacity of the object to be fired, etc.), and thus realise a cooling-down curve prescribed by the firing programme and not variable (which curve will then of course not progress in a linear fashion), wherein the IR camera merely detects the deviation below a temperature threshold. This temperature threshold is individual for the different materials used, such as, for instance, feldspar or lithium bi-silicate ceramics, and the type of firing (soldering, oxidising, glazing, etc.).

The invention claimed is:

1. Dental furnace comprising
a furnace base,
a furnace hood, wherein the furnace hood includes a firing chamber for the accommodation of dental restorations and a drive unit for the relative movement between the furnace hood and the furnace base, with a temperature sensor that records the temperature of the dental restorations and which is connected to a control device which controls the dental furnace,
wherein the control device controls the drive unit based on the temperature recorded by the temperature sensor and opens the furnace hood relative to the furnace base,
wherein the temperature sensor is an optical sensor and comprises a two-dimensional sensor array,
wherein the temperature sensor is positioned outside of the firing chamber,
wherein ambient temperature and dimensions of the dental restoration and/or a muffle which accommodates the dental restoration can be recorded with the aid of the temperature sensor, and
wherein the temperature sensor also records the presence or absence of the dental restoration and the moment of removal of the dental restoration and forwards a result of the recording to the control device, wherein the control device stores the result.

2. Dental furnace in accordance with claim 1, wherein the temperature sensor continuously records the temperature of the dental restoration, and wherein the control device calculates a temperature gradient from the continuously recorded temperature values of the temperature sensor.

3. Dental furnace in accordance with claim 1, wherein the optical sensor is an infrared sensor.

4. Dental furnace in accordance with claim 3, wherein the temperature sensor is a thermographic camera.

5. Dental furnace in accordance with claim 1, wherein the temperature sensor is positioned laterally above the furnace base.

6. Dental furnace in accordance with claim 1, wherein the furnace hood is provided with a window transparent for IR radiation which is positioned within the optical path between the dental restoration accommodated inside the firing chamber and the temperature sensor (20).

7. Dental furnace in accordance with claim 1, wherein the control device is suitable for controlling the cooling-down rate of the dental restoration by means of changing the position of the furnace hood relative to the furnace base with the help of the drive unit.

8. Dental furnace in accordance with claim 1, wherein a temperature of a carrier of the object to be fired can be recorded with the help of the temperature sensor.

9. Dental furnace in accordance with claim 1, wherein processing programs can be selected with the aid of an operation device, which processing programs can be stored in the control device, and wherein target values for a cooling-down rate of the dental restoration are predetermined in the processing programs.

10. Dental furnace in accordance with claim 1, wherein the control device is suitable for lowering the furnace hood if the cooling-down rate of the dental restoration is to high compared with a target value predetermined by a selected processing program, and wherin the control device is suitable for elevating or accelerating the furnace hood if the cooling-down rate of the dental restoration is too low compared with the target value predetermined by the selected processing program.

11. Dental furnace in accordance with claim 1, wherein a heating device is provided inside the furnace hood, and wherein the control device is suitable for switching on the heating device if the cooling-down rate of the dental restoration is too high compared with a target value predetermined by a selected processing program.

12. Dental furnace in accordance with claim 1, wherein a cooling device is provided at the dental furnace, and wherein the control device is suitable for switching on the cooling device if the cooling-down rate of the dental restoration is too low compared with a target value predetermined by a selected processing program.

13. Dental furnace in accordance with claim 1, wherein the dental furnace further comprises a signalling device connected to the control device, and wherein the control device is suitable via the signalling device to signal the deviation below a cooling-down temperature of the dental restoration part predetermined by a selected processing program.

14. Process for controlling a dental furnace, wherein the dental furnace is provided with a furnace base and a furnace hood which can be moved with the help of a drive unit, and the furnace hood includes a firing chamber for accommodation of dental restorations, and wherein the dental furnace is further provided with a temperature sensor which is connected to a control device and which is positioned outside the firing chamber, wherein the method comprises the following steps
the control device opens the furnace hood after expiry of a completed firing process corresponding to a predetermined value stored in the control device;
the temperature sensor records the temperature of the dental restoration; and
if the temperature of the dental restoration recorded by the temperature sensor falls below a value stored in the control device, the control device completely opens the furnace hood with the help of the drive unit and/or outputs a signal to the user via a signalling device connected to the control device, and
wherein the temperature sensor also records the presence or absence of the dental restoration and the moment of removal of the dental restoration and forwards a result of the recording to the control device, wherein the control device stores the result.

\* \* \* \* \*